United States Patent [19]
Roth et al.

[11] Patent Number: 6,095,578
[45] Date of Patent: Aug. 1, 2000

[54] DEVICES FOR HANDLING ITEMS WITH A HEAD AND A SHANK

[75] Inventors: Michael Roth, Ebringen; Paul Rath-Prazak, Breisach, both of Germany

[73] Assignee: Medartis AG, Basel, Switzerland

[21] Appl. No.: 09/052,693

[22] Filed: Mar. 31, 1998

[30] Foreign Application Priority Data

Apr. 5, 1997 [DE] Germany .............................. 197 14 055

[51] Int. Cl.[7] .................................................. B25C 3/00
[52] U.S. Cl. ............................................ 294/1.1; 221/157
[58] Field of Search .................................. 294/19.1, 1.1; 81/13, 44; 221/157, 171, 172, 312 C, 163, 250, 199, 226, 239, 307, 311

[56] References Cited

U.S. PATENT DOCUMENTS

| | | |
|---|---|---|
| 2,431,831 | 12/1947 | Sabaitis . |
| 2,775,766 | 1/1957 | Fenno . |
| 3,101,477 | 8/1963 | Leniz . |
| 3,472,356 | 2/1968 | Reppert ................................. 221/157 |
| 3,578,142 | 5/1971 | Burgess, Jr. ........................... 221/171 |
| 4,863,168 | 9/1989 | Anderka et al. ...................... 221/250 |
| 5,160,066 | 11/1992 | Hamuro et al. ...................... 221/172 |
| 5,219,198 | 6/1993 | Davis .................................... 294/19.1 |

FOREIGN PATENT DOCUMENTS

| | | |
|---|---|---|
| 0800796 | 10/1997 | European Pat. Off. . |
| 3930999 | 9/1989 | Germany . |
| 9303687 | 3/1993 | Germany . |
| 4407155 | 3/1994 | Germany . |
| 9412333 | 7/1994 | Germany . |

*Primary Examiner*—Dean J. Kramer
*Assistant Examiner*—Paul T. Chin
*Attorney, Agent, or Firm*—Selitto & Associates

[57] ABSTRACT

The device for handling items (20) with a head (21) and a shank (22), such as screws, pins and the like, has a hand piece (1), which has a chamber (2) for receiving the items (20). From an inner side (11) of the chamber (2) there extends a guiding recess (14,17) to a dispensing side (3) of the hand piece (1), which recess has a cross-section adapted to the outer contour of the items (20) and, at the end on the dispensing side, an end portion (18) angled away with respect to a delivery portion (19) adjoining the chamber (2). The items (20) can be transferred from the chamber (2) to the dispensing side (3), for example by tilting with respect to the horizontal, the angling away of the end portion (18) with respect to the delivery portion (19) having the effect of creating a dispensing block, ahead of which the items (20) build up in the dispensing direction. When the hand piece (1) is tilted over, the items can in each case leave individually one after the other the guiding recess (14,17) on the dispensing side (3) via the end portion (18).

19 Claims, 20 Drawing Sheets

DEVICES FOR HANDLING ITEMS WITH A HEAD AND A SHANK

FIELD OF APPLICATION OF THE INVENTION

The invention relates to devices for handling items with a head and a shank, such as screws, pins and the like, having a hand piece which has a chamber for receiving the items, there extending from an inner side of the chamber to a dispensing side of the hand piece a guiding recess which has a cross-section adapted to the outer contour of the items and, at the end on the dispensing side, has an end portion angled off with respect to a delivery portion adjoining the chamber.

PRIOR ART

Such a device is known from U.S. Pat. No. 3,101,477. In the case of this device for handling drawing pins with a head and a shank, a hand piece which has a chamber for receiving the drawing pins is provided. From the inner side of the chamber to a dispensing side of the hand piece there extends a guiding recess which has a cross-section adapted to the outer contour of the drawing pins and, at the end on the dispensing side, has an end portion angled off with respect to a delivery portion adjoining the chamber. The delivery portion merges at one end with the chamber by a rounding off, while its other end is adjoined by a rounded-off transitional region with respect to the straight-running end portion. Furthermore, the device of the generic type has a slide which is designed in the manner of a knob and is displaceable along the guiding recess from the delivery portion through the rounded-off transitional portion in the direction of the end portion. The slide serves for transferring drawing pins out of the chamber into the end portion. However, for dispensing individual drawing pins, the device of the generic type requires the slide and also a relatively complex-to-produce arrangement of feed slots in the entry region of the delivery portion into the chamber.

U.S. Pat. No. 2,431,831 discloses a device for handling pins with a head and a shank which has a storage chamber which is fastened to a carrying part and which can be filled with the pins. The storage chamber is adjoined by a guiding recess, which is bounded by two side parts and has a delivery portion flush with the bottom of the storage chamber and an end portion in connection with the delivery portion via a transitional portion bent in the shape of an S. In this case, the storage chamber, the delivery portion and the end portion are arranged approximately equally inclined with respect to the vertical and the S-shaped transitional portion is aligned such that its central part is inclined more in the direction of the vertical than are the delivery portion and the end portion. At an end of the end portion on the dispensing side there is provided a mechanism for removal of the pins. However, this device is not set up for dispensing individual items directly from the end of the end portion on the delivery side.

U.S. Pat. No. 2,775,766 discloses a device for handling pins with a head and a shank which has a number of tube parts running parallel to one another and spaced apart from one another at the thickness of the pin shanks. At an end of the device on the dispensing side, the tube parts have a bevel. Pins can be introduced between the tube parts, the shanks extending through the constriction between the tube parts and the heads being arranged in a widened region between the tube parts. By tipping the device with respect to the horizontal, the pins slide between the tube parts in the direction of their ends on the dispensing side, the bevel provided there causing the said pins to be tilted, while held back by a cross-piece in the region of the shanks, and to be removable by hand.

DE-U-93 03 687 discloses a handling aid for quick-assembly screws, which has a holding part which can be pushed on by the fingers. The holding part has two magnetic strips running parallel to each other, to which metallic quick-assembly screws can attach themselves. Between the magnetic strips there extends a T-shaped groove, into which there can be pushed a magazine strip, to which the quick-assembly screws are fastened by means of lugs. The holding part has at the end on the dispensing side a hollow into which a shank of an item to be held can be inserted.

DE-A-39 30 999 discloses a feeding device for an appliance which is preferably to be fastened to a robot and is intended for driving in fastening means, in which device fastening means introduced into a guiding recess can be transferred by a chain mechanism around a deflection roller of the chain mechanism to a dispensing side. On the dispensing side there is provided, for example, a screwing tool.

DE-U-94 12 333 discloses a pin and screw holder in the form of pincers which have notches for receiving pins or screws milled into their gripping jaws. For securely holding the items to be handled, a compression spring which presses the gripping jaws together is provided.

Further conventional devices for handling in particular relatively small items having a head and a shank, such as screws, pins and the like, are designed for example as tweezers with which an item can be gripped by the tips of the tweezers in the region of the shank or the head and can be inserted for example into one of a plurality of screw-receiving recesses of a screw-receiving part which are arranged in a grid-like manner, as used in the field of surgery for keeping bone screws ready during an operation. It is true that in principle these devices can be used for handling items with a head and a shank. However, the inserting of in particular small items into the screw-receiving recesses of a screw-receiving part, for example, is very time consuming and requires a concentrated, manually skilled way of working. After labouring for many hours in an operating theatre, this may only be possible to a limited extent.

OBJECT OF THE INVENTION

The invention is based on the object of providing devices of the type mentioned at the beginning with which items which have a head and a shank can be reliably handled by simple manipulations—even under aggravated working conditions.

SUMMARY OF THE INVENTION

This object is achieved according to the invention in the case of a device of a first type in that the end portion, at least in its region adjoining the delivery portion, is aligned at an acute angle with respect to the delivery portion and runs at an inclination counter to the feeding direction of an item from the chamber into the front region of the delivery portion adjoining the end portion, and consequently in the direction of the delivery portion.

The fact that, in the case of the device of the first type, the end portion is aligned at an acute angle with respect to the delivery portion and runs at an inclination in the direction of the delivery portion has the effect of creating a dispensing block, which prevents items from sliding out, for example if the hand piece is tilted in an uncontrolled manner with respect to the horizontal. The dispensing of items only takes place after controlled handling, by the items being guided around the angled-away portion.

The object is achieved according to the invention by a device of a second type in that the end portion, at least in its region adjoining the delivery portion, is aligned at right angles with respect to the delivery portion and in that, in the transitional region between the delivery portion and the end portion, a blind continuation extending in prolongation of the end portion and/or a depression lying opposite the delivery portion are provided as a head-engaging means.

The right-angled alignment of the end portion with respect to the delivery portion and the provision of a blind continuation and/or a depression have the effect that a head of an item can slide in the transitional region from the delivery portion into the end portion in an engaging manner, with the result that both the unintentional slipping thereafter of following items is blocked and unintentional losing of the items is prevented. Only after a controlled dispensing movement is the front item discharged from the end portion, the following item then sliding into the blind continuation and/or the depression.

The provision of a hand piece which has a chamber for receiving the items, it being possible for the items to be transferred to the dispensing side via the guiding recess adapted in contour to the items and with an angled-away end portion, has the effect that reliable handling with simple manipulations is achieved by the fact that the chamber can be filled with a certain following item then sliding into the blind continuation and/or the depression.

The transfer of the items from the delivery portion into the end portion is facilitated by the provision of a curved transitional portion, without the effect of the angled-away portion as a dispensing block being adversely affected.

To be able to use a hand piece to handle items with shanks of different lengths and/or diameter, but other-wise the same outer contour in the region of the heads, it is expedient for the part of the guiding recess receiving the shanks to be open towards the side of the hand piece lying opposite the chamber.

In order that the items can be inserted reliably into the guiding recess, it is expedient for the guiding recess to adjoin the base of the chamber, the chamber base being of an acute-angled design. In order that no instances of jamming occur in the entry region of the delivery portion of the guiding recess of the chamber, it is expedient to design the guiding recess such that it is widened in the entry region into the chamber.

If a number of items exceeding the capacity of the delivery portion between the chamber and the end portion are to be introduced into the chamber, it is expedient to provide a cover with which the chamber can be closed. Further expedient developments and advantages of the invention are defined in the dependent claims.

The production of the hand piece is significantly simplified by the hand piece being made up of two hand piece parts which can be fitted together. An essential number of items and the fact that the items can be transferred into the delivery portion of the guiding recess in a series arrangement up to the angled-away end portion, for example by tilting with respect to the horizontal. The items arranged in series can be individually guided one after the other around a dispensing block formed by the angled-away portion, for example by tilting the hand piece, with the result that dispensing which can be controlled by simple manipulations is provided, for example for inserting the items into screw-receiving recesses of a screw-receiving part.

In the case of an expedient development, the dispensing side of the hand piece is of a tip-like design, with the result that the items can be inserted even under relatively confined conditions, for example in screw-receiving recesses which are close together. To provide an effective dispensing block, it is expedient for the delivery portion and the end portion to be aligned at an acute angle with respect to each other in the region where they meet. The controlled dispensing from the end portion is facilitated by an end portion curved in the direction of the delivery portion, by the hand piece being handled in a rolling-like movement.

It is expedient to provide in the acute-angled transitional region between the delivery portion and the end portion a blind continuation extending in prolongation of the end portion and/or a depression in the end portion, into which a head of an item can slide in an engaging manner, with the result that both the unintentional slipping thereafter of following items is blocked and unintentional losing of the items is prevented. Only after a controlled dispensing movement is the front item discharged from the end portion, the advantage of the devices according to the invention is, in particular, that, when refilling, the items to be handled—for example implant screws—are emptied straight from the pack into the filling chamber. Any outside contact, for example with the hands or tweezers, is unnecessary. This excludes the risk of contamination or of damaging the surface of the items to be handled. In the devices according to the invention, there are no moving device parts which could cause damage to the surface of the items to be handled.

DETAILED DESCRIPTION OF EXEMPLARY EMBODIMENTS

Figure 1:
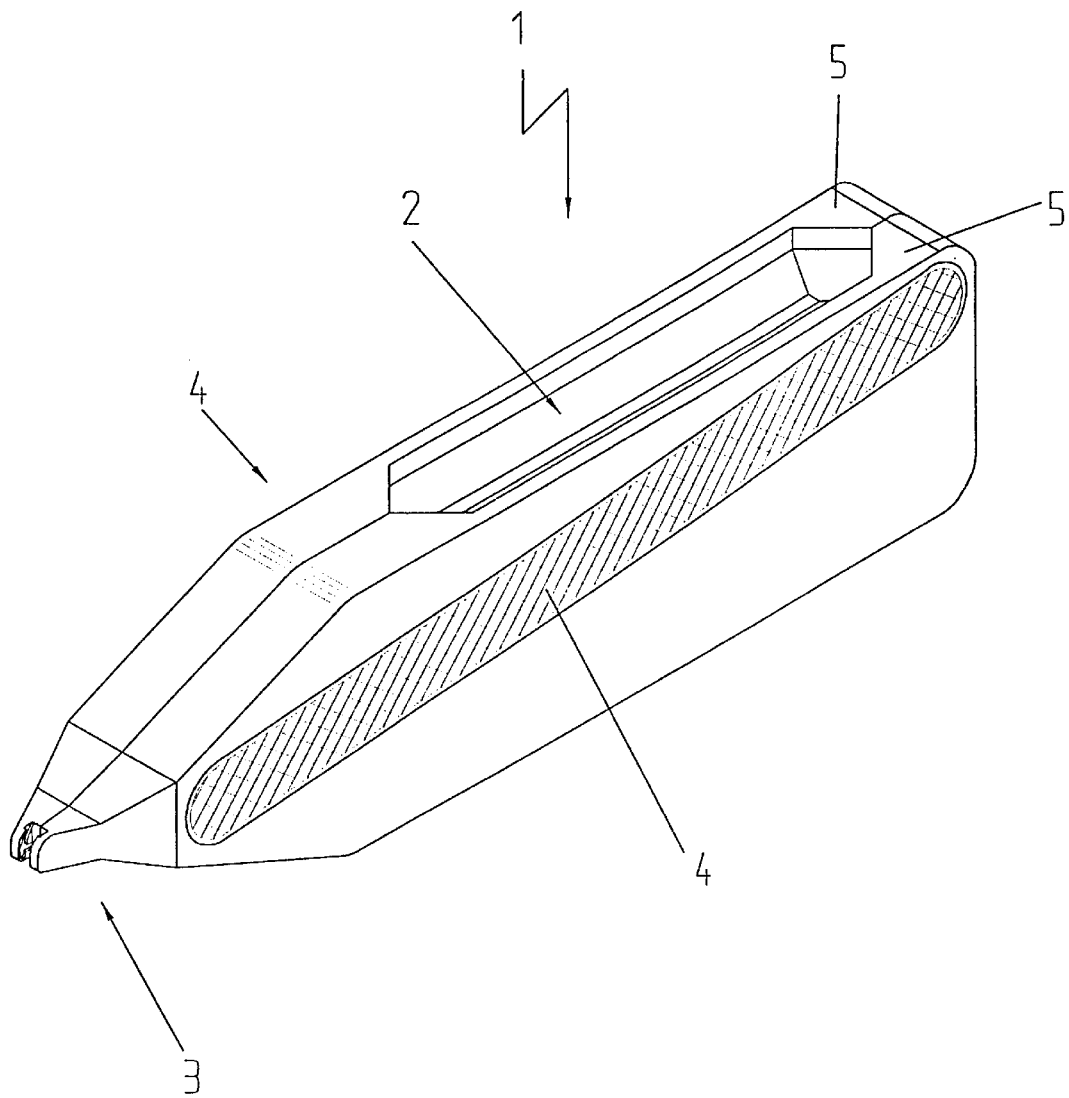
FIG. 1: shows as a perspective view a device according to the invention with a hand piece which is composed of two hand piece parts and has a filling chamber, which remains open, and a hand piece tip formed on a dispensing side.
Figure 2:
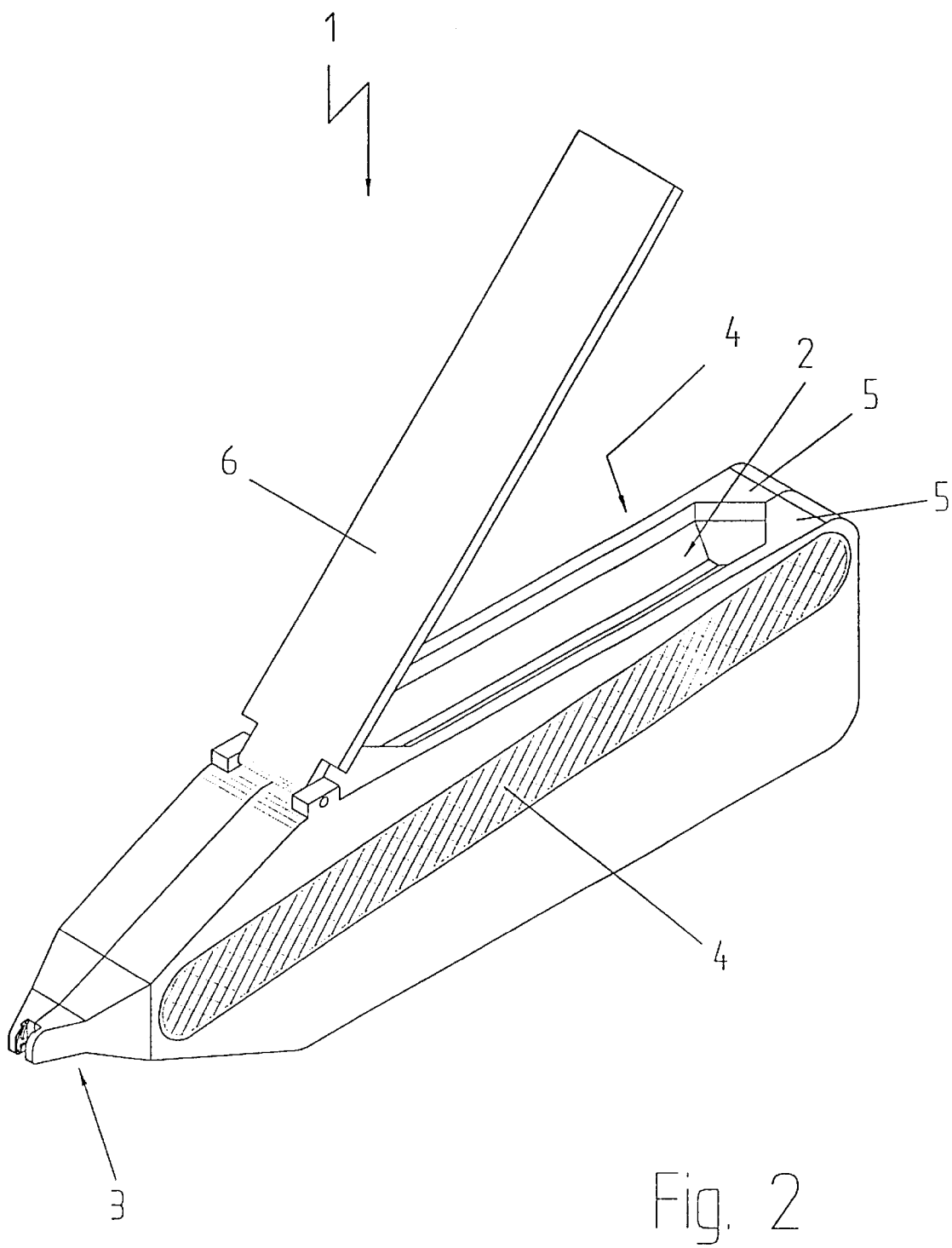
FIG. 2: shows as a perspective view the device according to FIG. 1 with a closable filling chamber.

With reference to the figures, preferred exemplary embodiments of devices according to the invention are described below.

FIG. 1

The hand piece 1 is of an elongated cuboidal design in the region of a filling chamber 2, as a chamber, and is of a tapering design in the region of a hand piece tip 3, as a dispensing side. Here, the filling chamber 2 is of a design which remains open. Applied to side faces of the hand piece 1 are gripping strips 4, which have a surface which has elevations and depressions and are expediently coloured, in order to indicate to a user the application range of the hand piece 1—for handling for example screws of a certain size. The hand piece 1 is made up of two hand piece parts 5 which can be fitted flush together.

FIG. 2

On the developed hand piece 1 there is attached a preferably transparent hinged cover 6 for closing the filling chamber 2. The embodiment of this hand piece 1 is expedient in particular in applications in which a number of items introduced into the filling chamber 2 remain in it during handling, since the hinged cover 6 in the closed position prevents falling out of the items remaining the filling chamber 2.

FIG. 3

The hand piece part 5 shown here has devices 7 for the aligned connection of the two hand piece parts 5. The devices 7 are formed for detachable screwing—for example by means of projections engaging in alignment recesses for accurately fitting alignment and by means of fastening recesses with opposite internal threaded portions.

For forming the filling chamber 2, the hand piece parts 5 are provided in their mutually facing inner side face 8 with filling-chamber recesses which are bounded—for example by a parallel-wall portion 9, aligned parallel to the inner side face 8, and an oblique-wall portion 10, extending between the parallel-wall portion 9 and the inner side face 8—with the result that the filling chamber 2 is of a tapering design at the bottom inner edge 11 and the side inner edges 12.

The tapering angle is designed such that, with a substantially horizontal alignment of the bottom inner edge 11, items with head and shank introduced into the filling chamber 2 come to lie in the filling-chamber base 13 of their own accord due to the effect of gravity. For example, the tapering angle lies between about 60° and about 120°, preferably between about 80° and 100°.

Furthermore, each hand piece part 5 is provided with a head-guiding groove 14 of a guiding recess, which groove extends from the filling chamber 2 to the hand piece tip 3 and also extends along the filling-chamber base 13 of the filling chamber 2 and is arranged such that the bottom inner edge 11 of the filling chamber 2 is open with respect to the head-guiding groove 14 in the region of the filling-chamber base 13. It is expedient for the head-guiding groove 14 to be widened in cross-section in the entry region 15 into the filling chamber 2 by means of an introductory rounding-off 16 to facilitate the entry of a head of an item.

Each hand piece part 5 has on the side of the head-guiding groove 14 lying opposite the filling chamber 2 a shank-guiding recess 17 of a guiding recess, which extends up to the outer side of the hand piece parts 5 lying opposite the filling chamber 2 and adjoins the head-guiding groove 14. The shank-guiding recess 17 extends along the head-guiding groove 14 into the hand piece tip 3 and is set back from the inner side face 8 by an offset which is less than the depth of the head-guiding groove 14.

In the region of the hand piece tip 3, the head-guiding groove 14 has an angled-away end portion 18, which is aligned here at an acute angle with respect to a delivery portion 19 extending between the filling chamber 2 and the end portion 18, the end portion 18 and the delivery portion 19 being designed in the region where they meet such that there is formed a dispensing block, which prevents items from leaving of their own accord the guiding recess formed by the head-guiding grooves 14 and the shank-guiding recesses 17.

FIG. 4

The hand piece 1, comprising the joined-together hand piece parts 5, with the filling chamber 2 can be seen. In the filling-chamber base 13, a bearing face for the heads of the items to be handled is created by the shoulders formed as a transition from the head-guiding grooves 14 to the shank-guiding recesses 17, while the shank-guiding recesses 17 allow the entry of shanks of the items.

FIG. 5

It can be seen that the shank-guiding recesses 17 extend over the entire length of the head-guiding groove 14 from the filling chamber 2 into the hand piece tip 3.

FIG. 6

It can be seen how the head-guiding grooves 14 and the shank-guiding recesses 17 of the hand piece parts 5 complement one another to form the guiding recess, the cross-section of which is adapted to the outer contour of the items to be handled.

Figure 7:
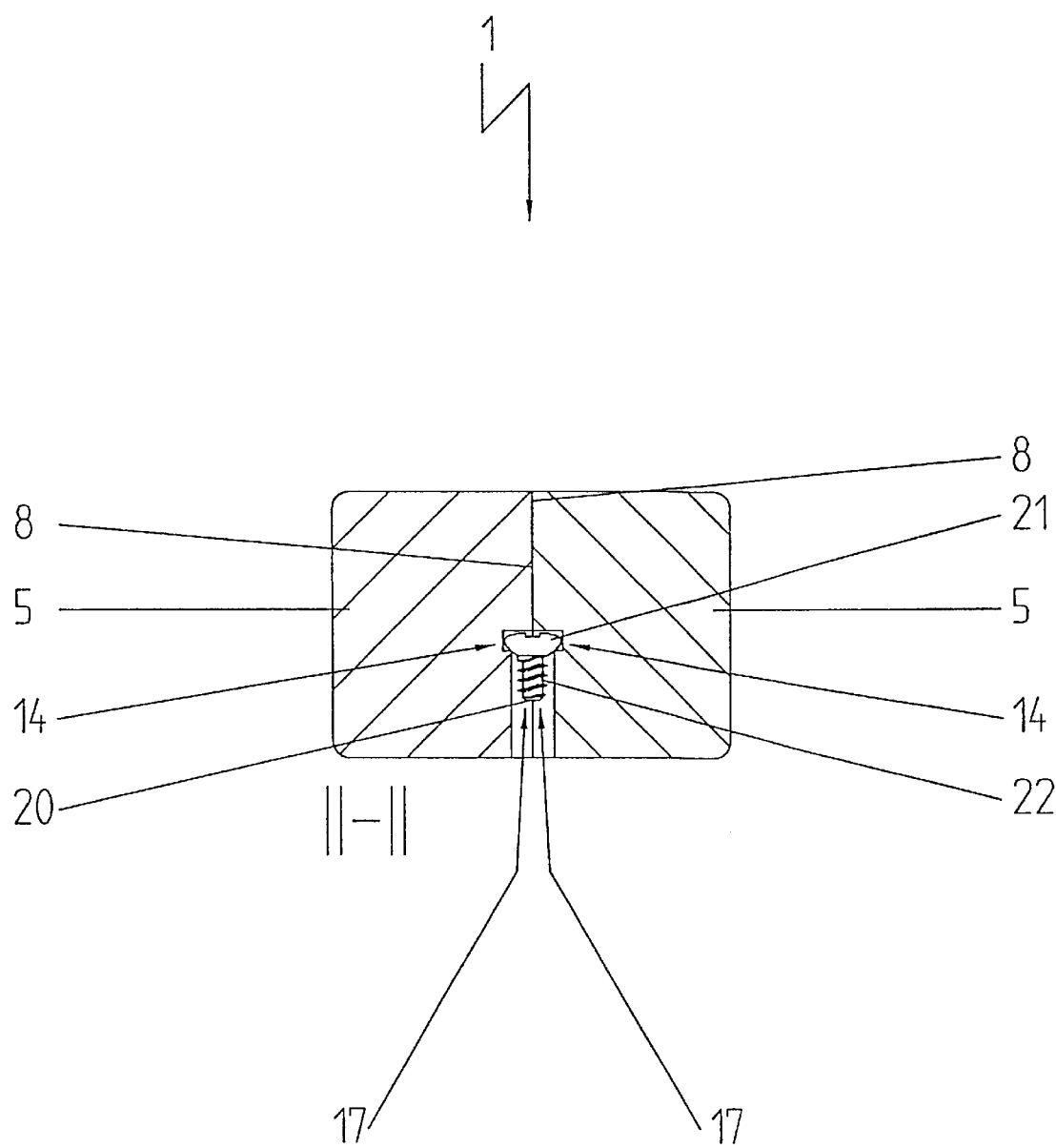

FIG. 7 In the case of this exemplary embodiment, a screw 20 is located in the hand piece 1. The screw head 21 bears against the shoulders formed between the head-guiding grooves 14 and the shank-guiding recesses 17, while the screw shank 22 has entered the shank-guiding recesses 17. The screw 20 is guided with slight play by a guiding recess with a cross-section which is adapted to the outer contour of the screw 20. This guiding recess is formed by the head-guiding grooves 14 and the shank-guiding recesses 17.

FIG. 8

In the transitional region between the delivery portion 19 and the end portion 18 of the head-guiding groove 14 curved counter to the feeding direction of an item from the filling chamber 2 into the front region of the delivery portion 19 adjoining the end portion 18—thus in the direction of the delivery portion 19—there is formed in prolongation of the end portion 18 a blind continuation 23, which is aligned substantially at right angles with respect to the delivery portion 19. The end portion 18 is enlarged with a depression 24 in a region lying opposite the delivery portion 19. Furthermore, between the end portion 18 and the delivery portion 19 of the head-guiding groove 14 there is provided in the inner side face 8 a transitional recess 25, the depth of which preferably corresponds to the depth of the shank-guiding recess 17.

FIG. 9

A bearing side 26 of the hand piece tip 3 is designed such that it corresponds to the shape of the end portion 18 of the head-guiding groove 14, with the result that there is a substantially constant residual material thickness between the end portion 18 and a front outer side 27 of the hand piece 1 in the region of the bearing side 26.

FIG. 10

The head-guiding groove 14 situated between the end portion 18 and the delivery portion 19 has a substantially constant cross-section and inner side faces 8 which lie in surface contact on one another even in the intermediate region between the end portion 18 and the delivery portion 19. A transitional region 28 between the end portion 18 and the delivery portion 19 of the head-guiding groove 14 is of a round design, the end portion 18 being curved in the case of this modification as well.

FIG. 11

Here, the end portion 18 is of a straight design.

FIG. 12

Figure 8:
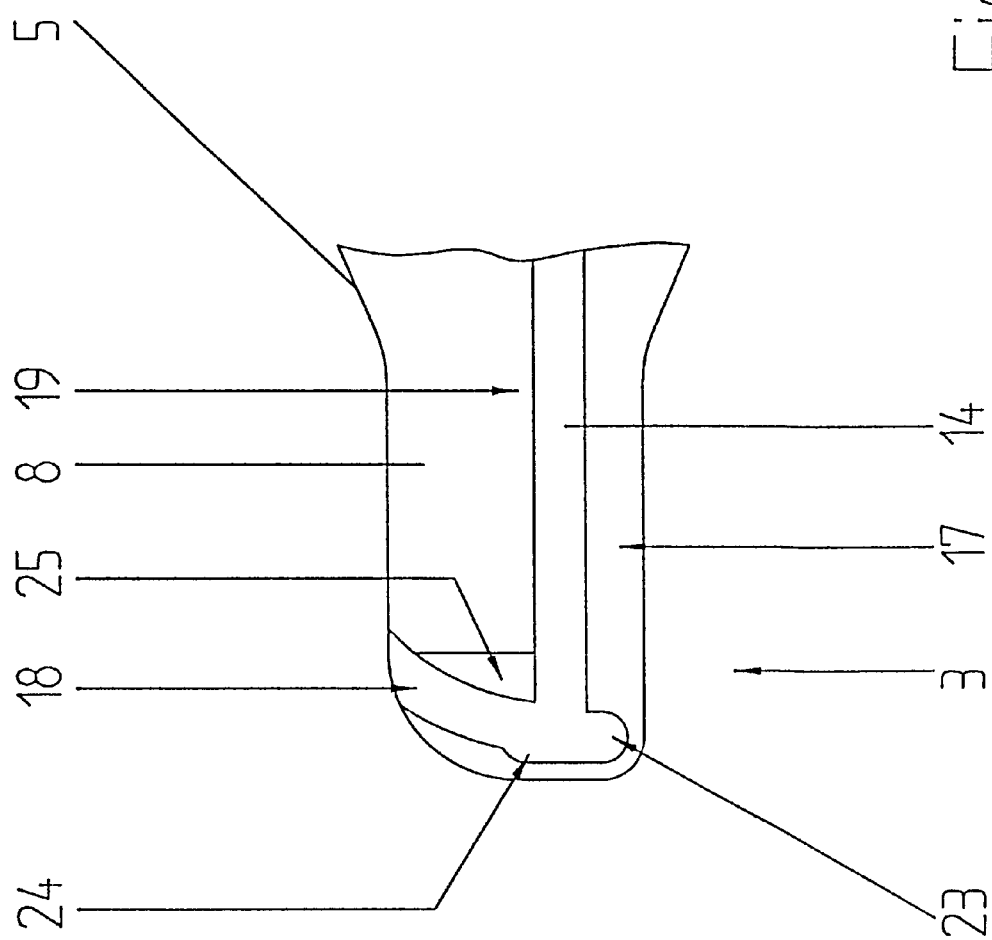
Figure 9:
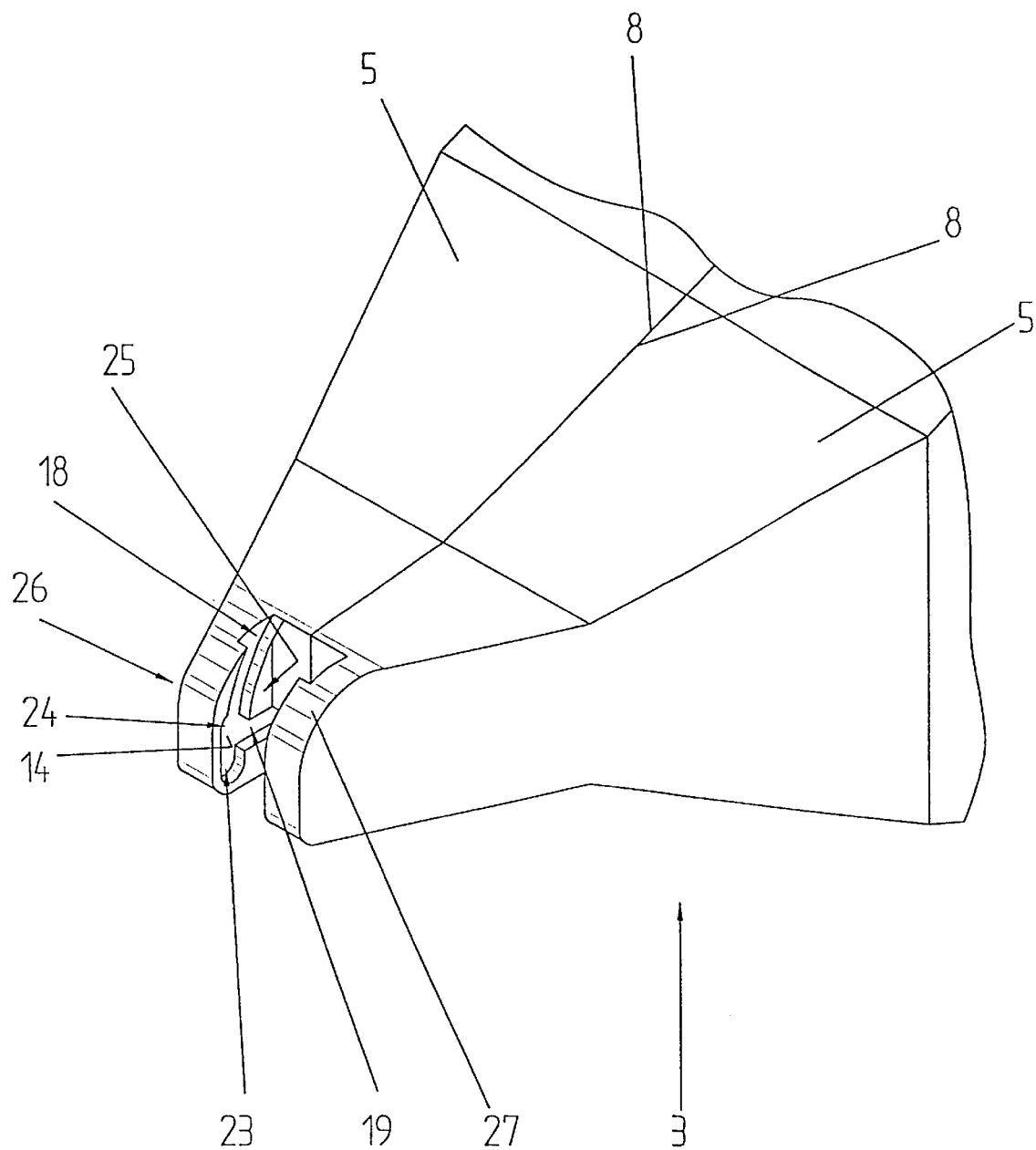
FIG. 9: shows as an enlarged perspective representation the hand piece tip of the device according to FIG. 1, FIG. 10: shows as a side view a further modification of the hand piece tip.
Figure 10:
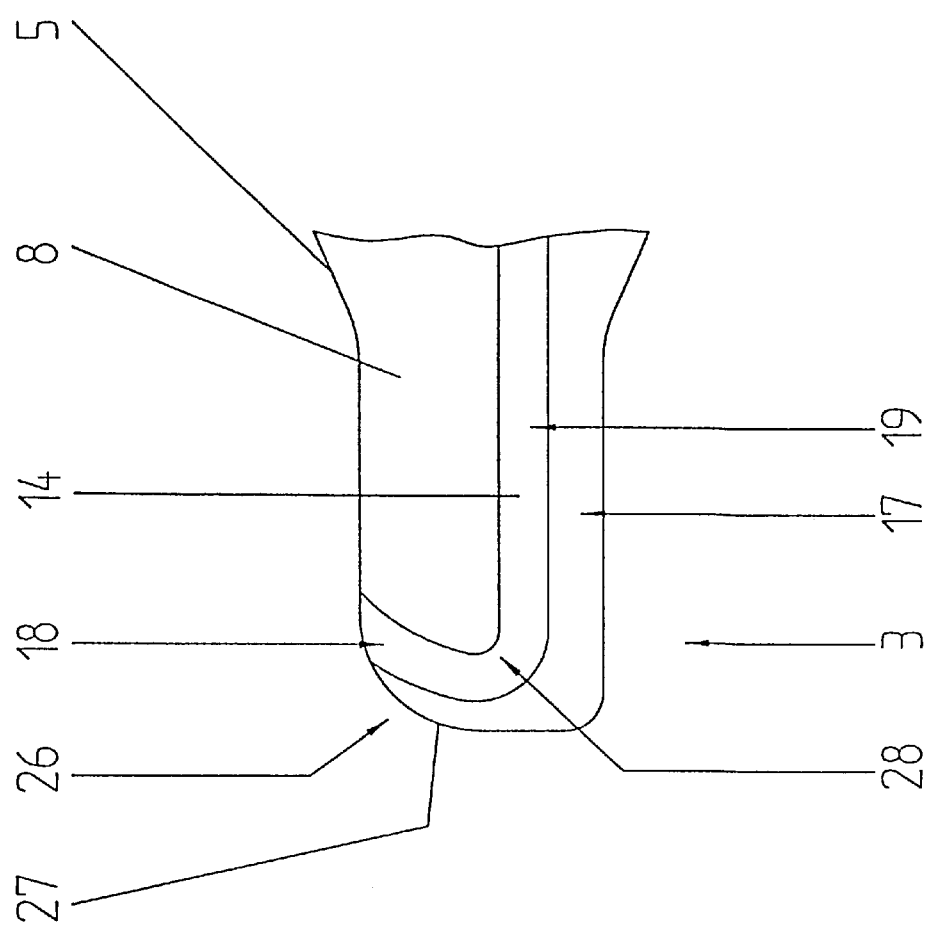
Figure 11:
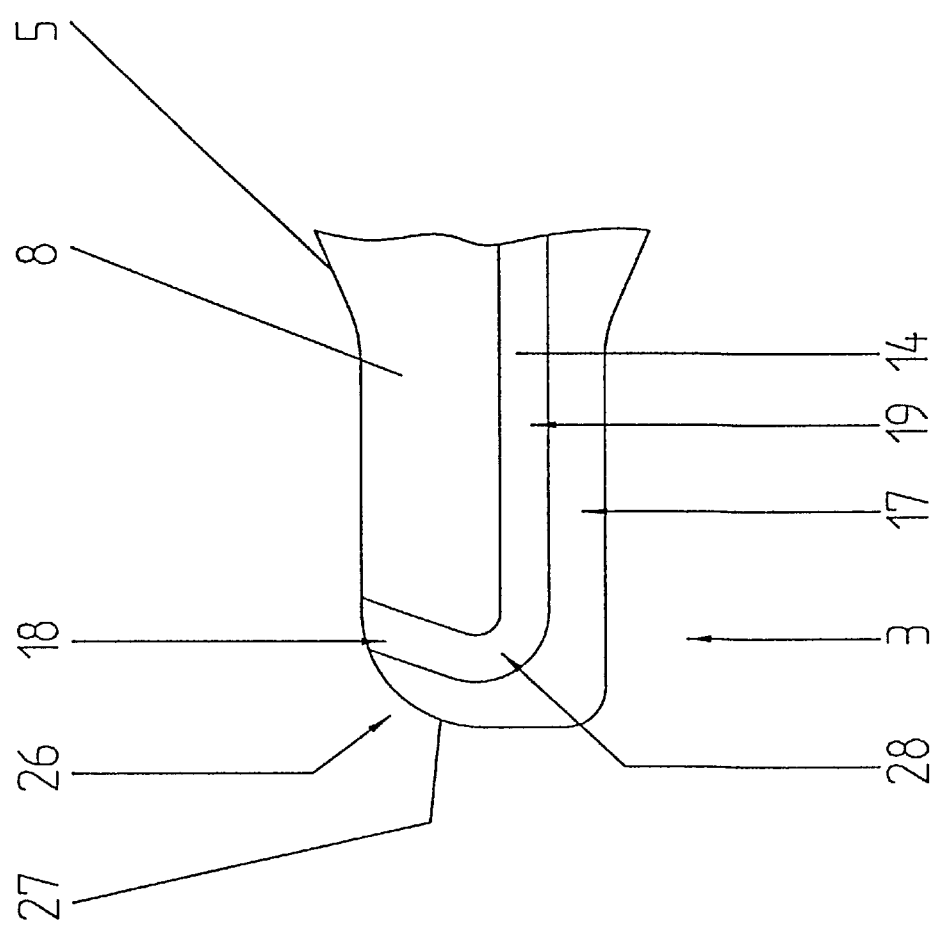
FIG. 11: shows as a side view the hand piece tip with an end portion of a straight design.
Figure 12:
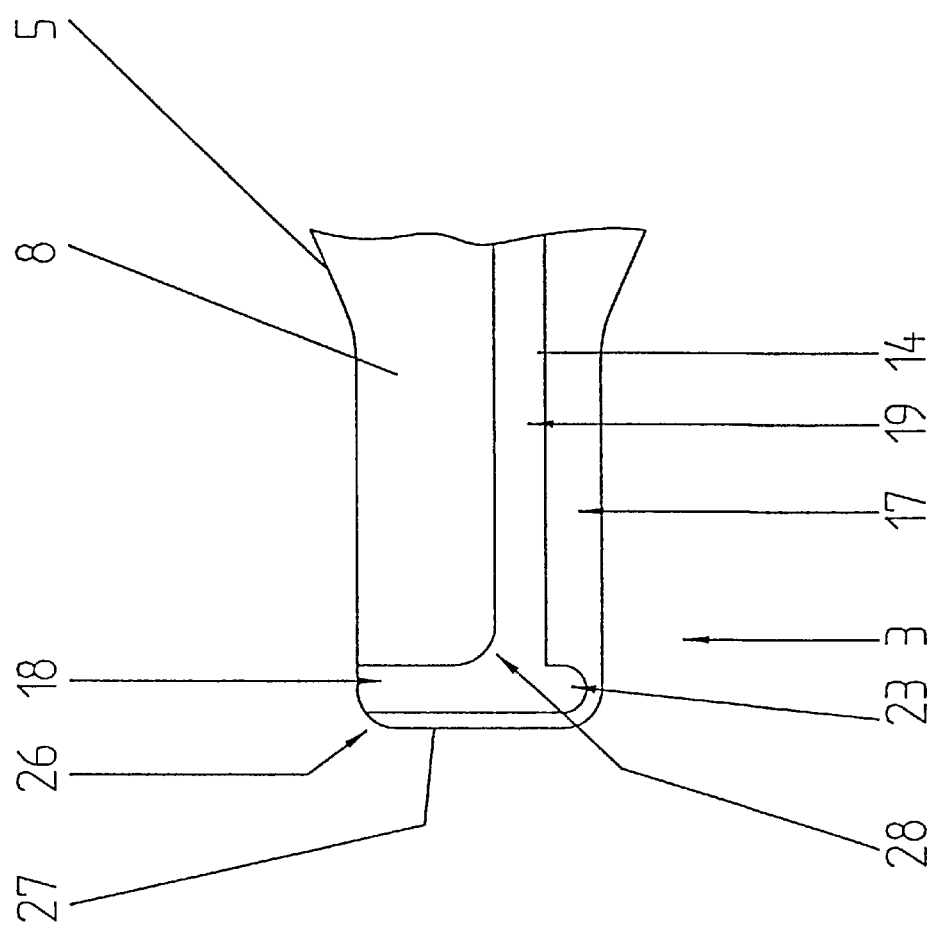
FIG. 12: shows as a side view the hand piece tip with the end portion and the delivery portion aligned at right angles with respect to each other.
Figure 13:
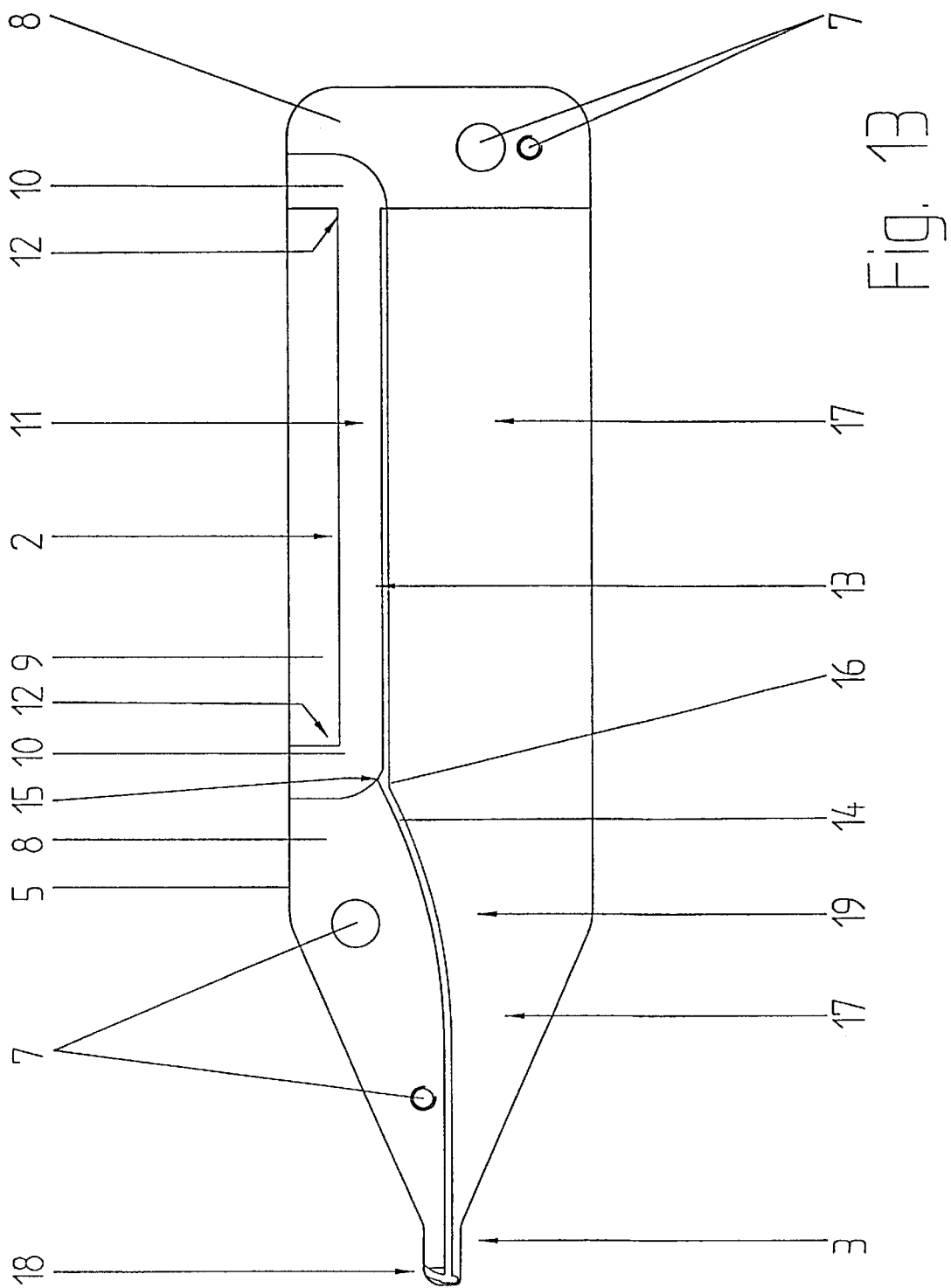
FIG. 13: shows as a side view a hand piece part with a filling chamber made less deep than in the case of the device according to FIG. 1, FIGS. 14 to 18: show as side views a hand piece part for explaining the handling of the hand piece according to FIG. 1 when inserting screws into a screw-receiving part.
Figure 14:
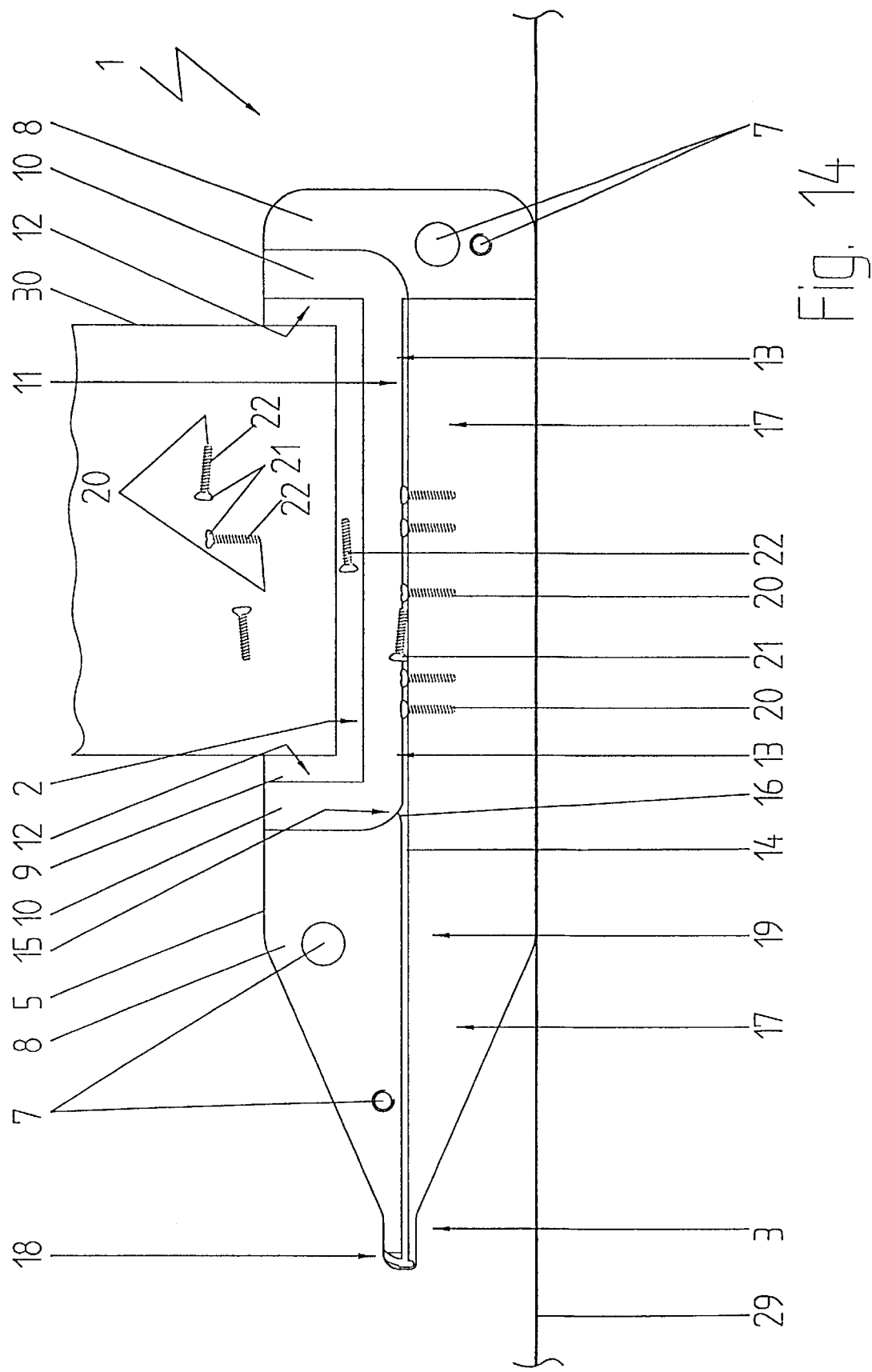
Figure 15:
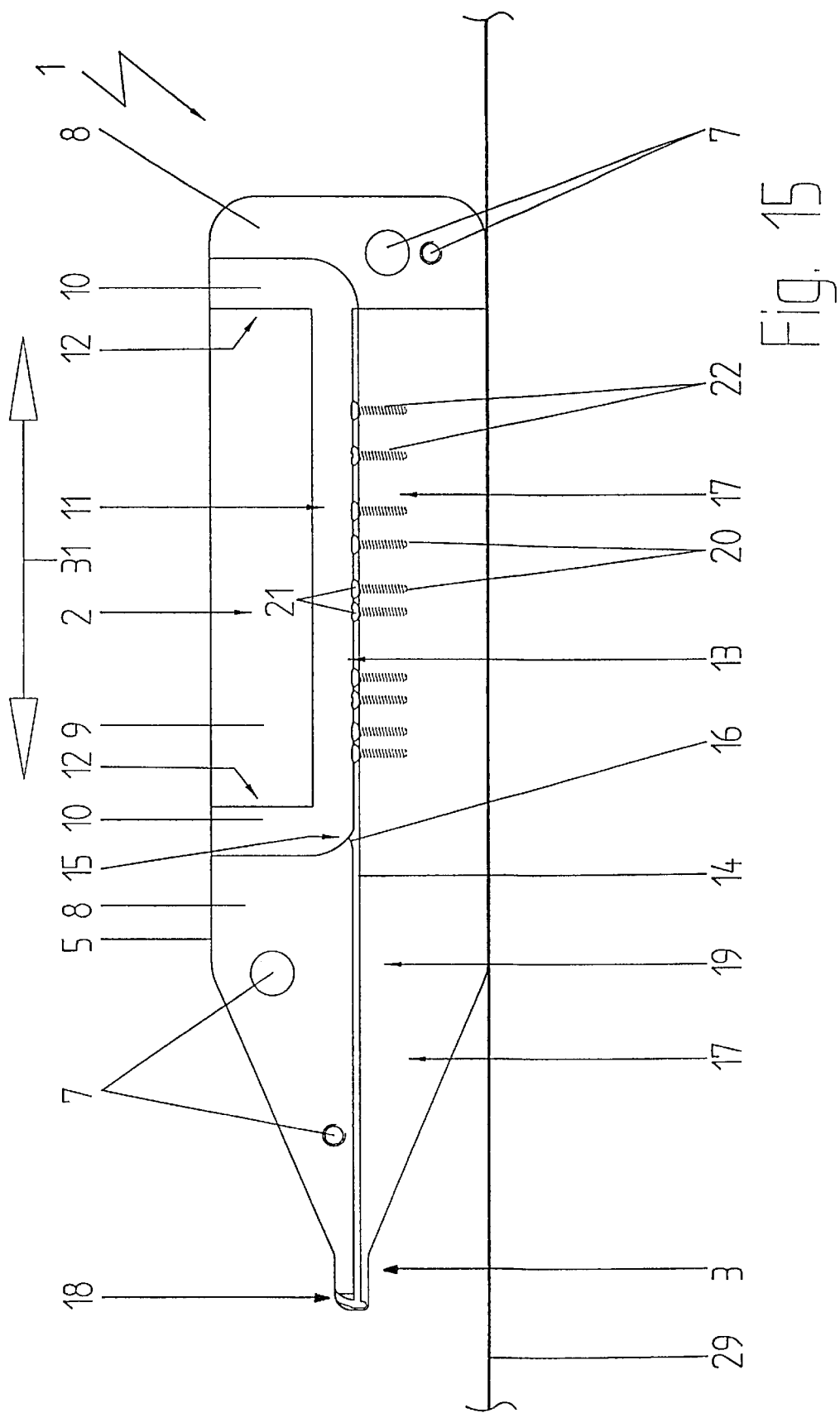
Figure 16:
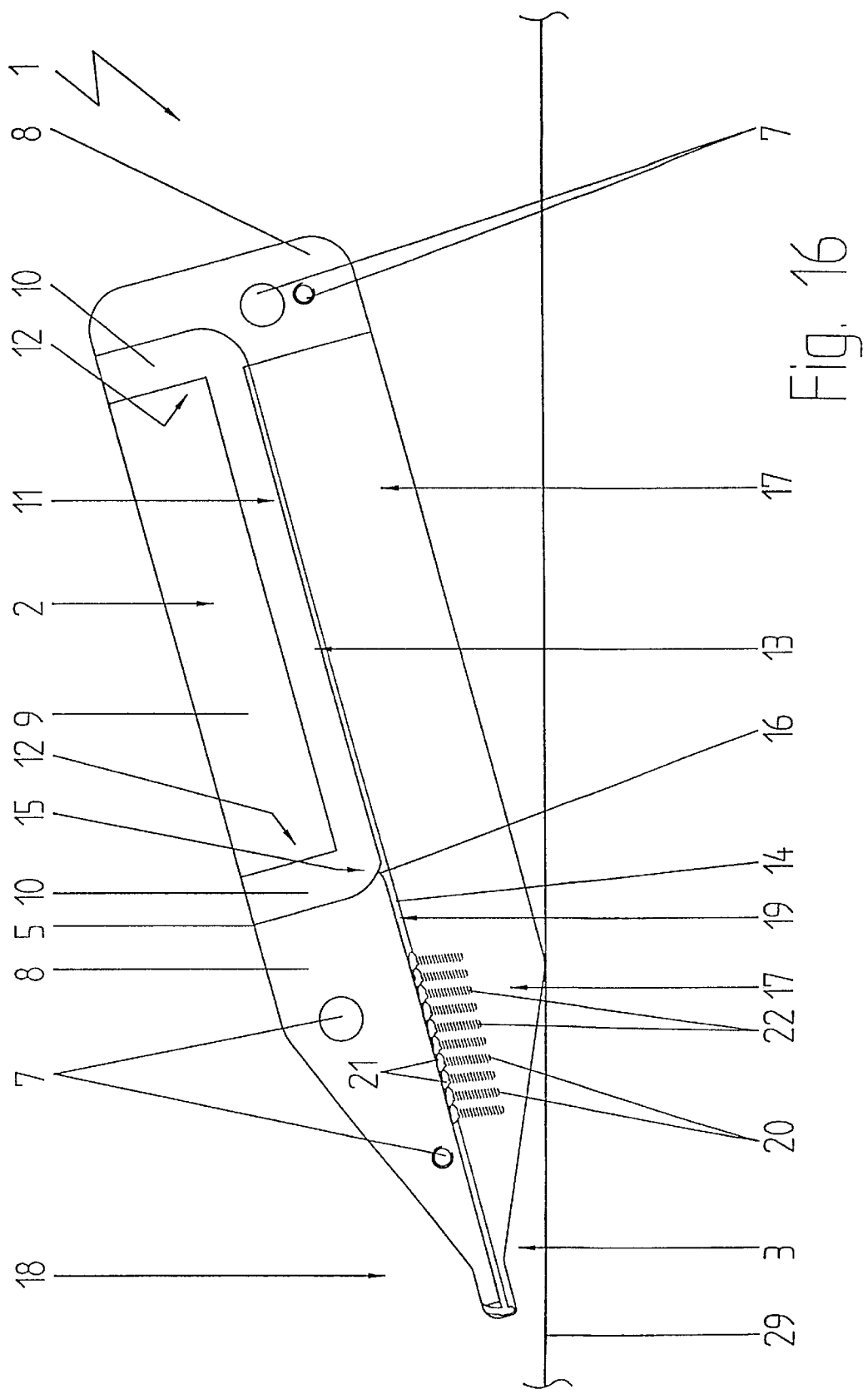

In the case of this modification, the end portion 18 and the delivery portion 19 are aligned at right angles with respect to each other, the end portion 18 being of a straight design. In a way corresponding to the configuration according to FIG. 8, lying opposite the end portion 18 there is formed a blind continuation 23 adjoining the delivery portion 19. The inner side faces 8 of the hand piece parts 5 bear flat against one another up to the head-guiding groove 14, the averted wall of the head-guiding groove 14 lying opposite the blind continuation 23 forming a semilaterally curved transitional region 28.

FIG. 13

Figure 3:
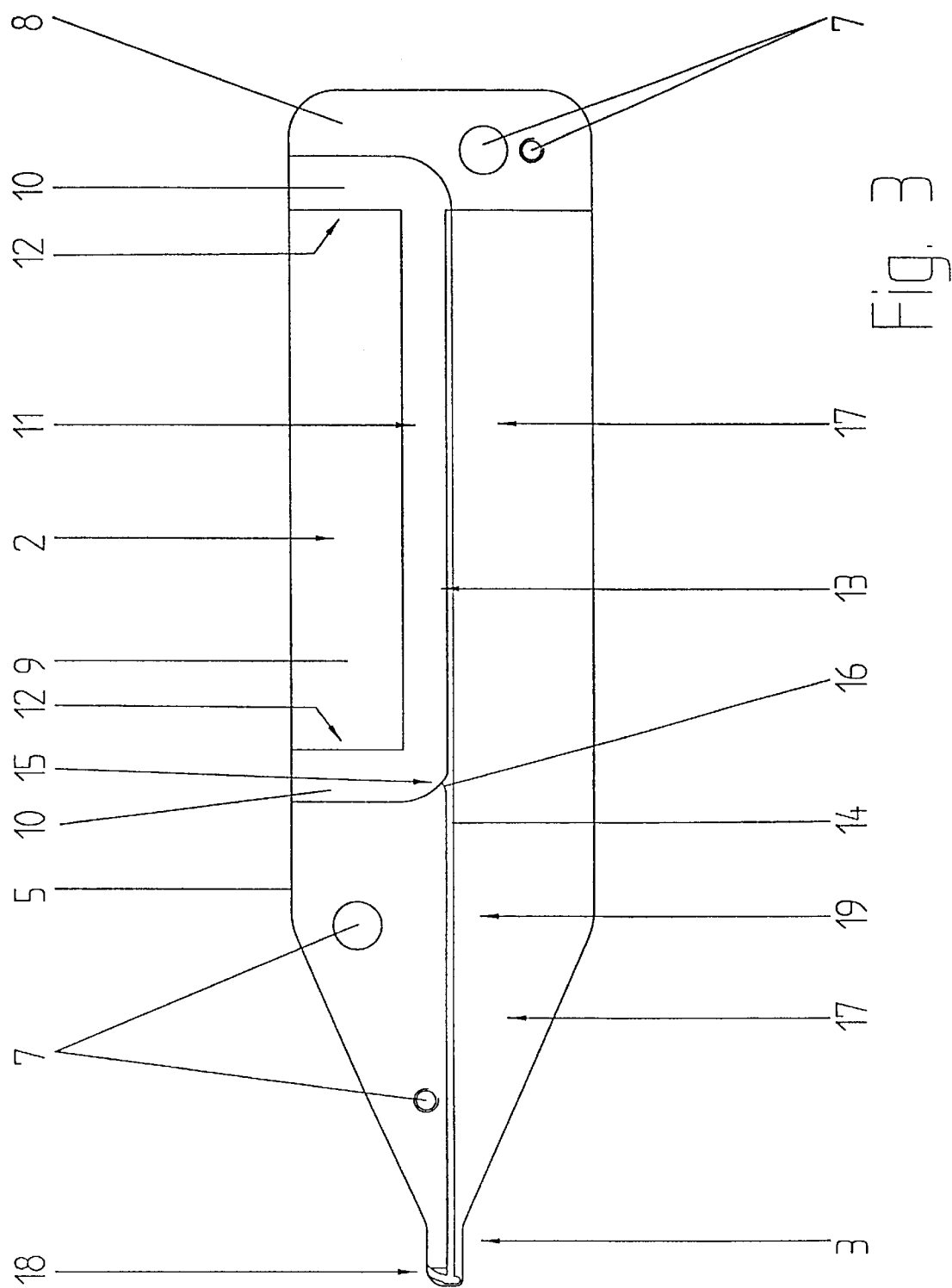
FIG. 3: shows as a side view a hand piece part of the device according to FIG. 1 with a guiding recess extending between the filling chamber and the hand piece tip.
Figure 4:
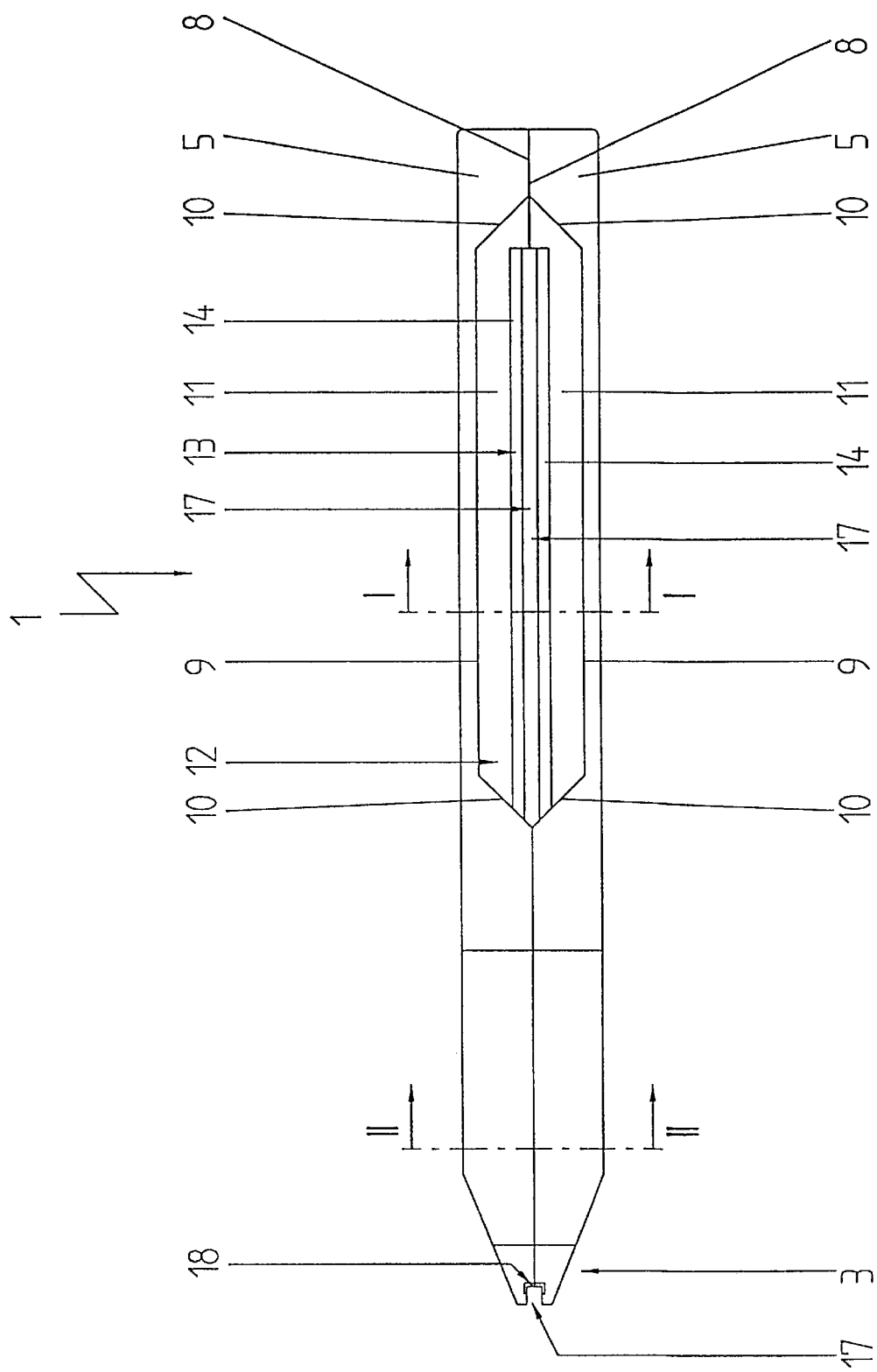
FIG. 4: shows as a plan view the filling chamber of the device according to FIG. 1, FIG. 5: shows as a plan view the hand piece according to FIG. 1, on the side lying opposite the filling chamber.
Figure 5:
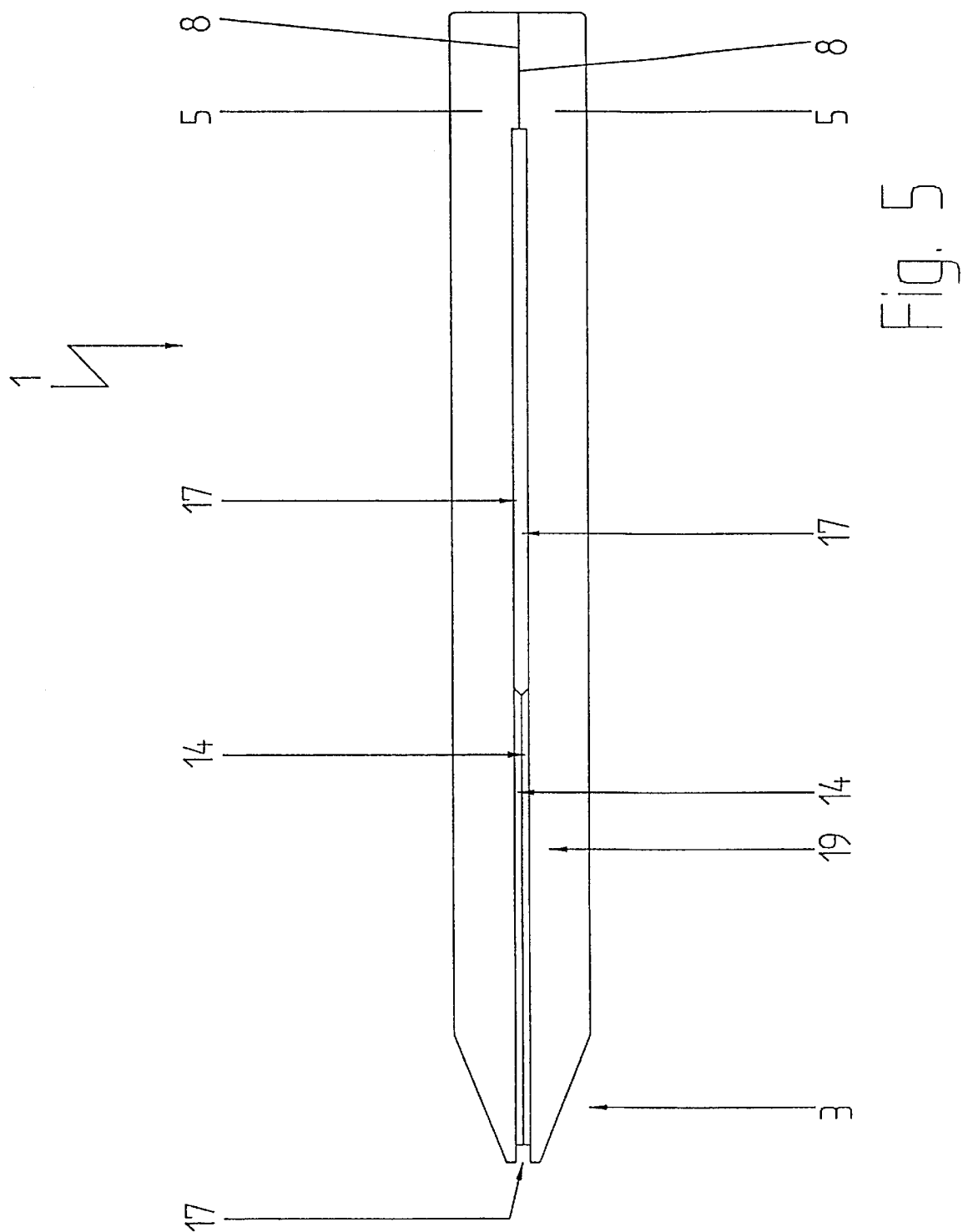
Figure 6:
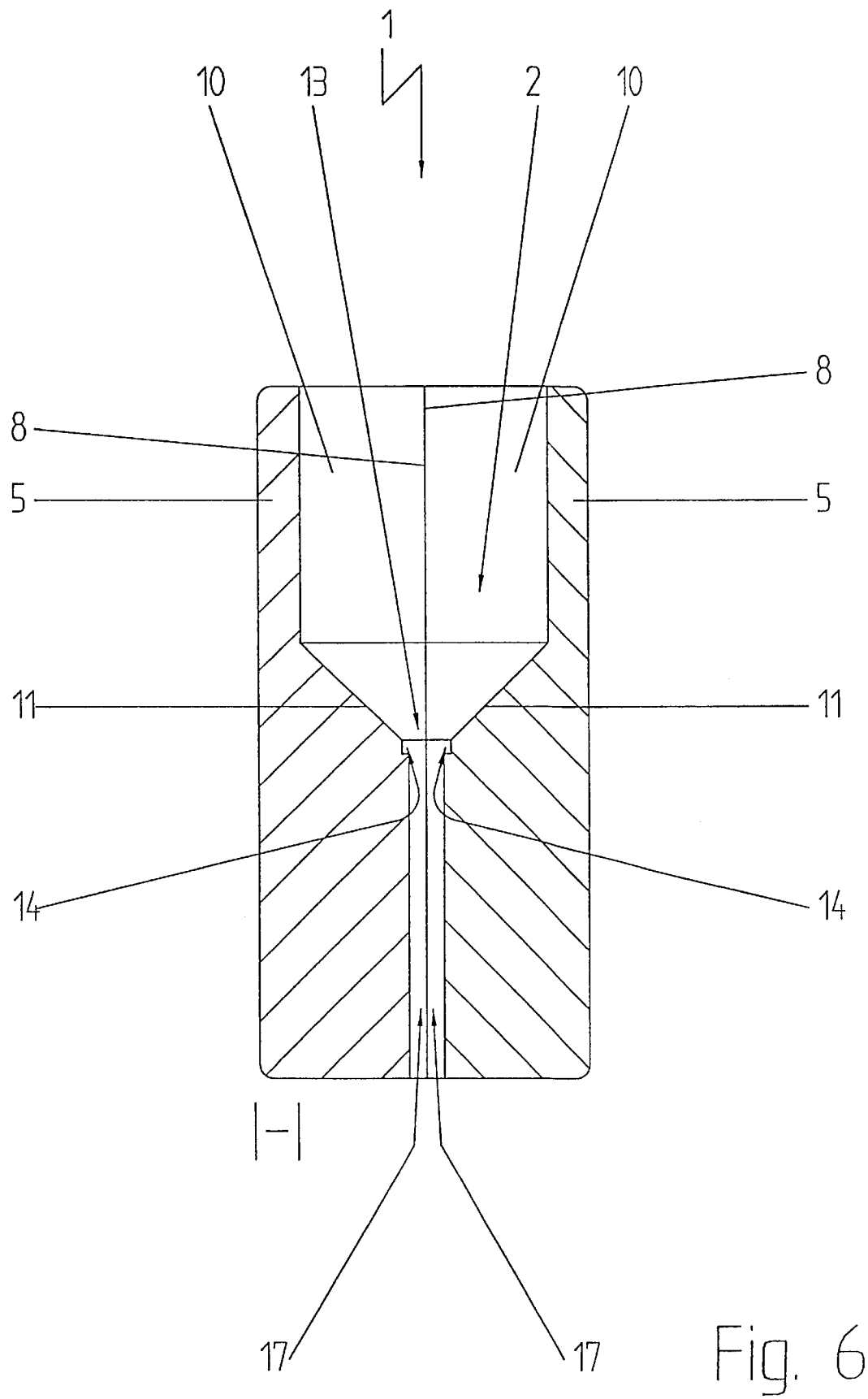
FIG. 6: shows a section along the line I—I according to FIG. 4, FIG. 7: shows a section along the line II—II according to FIG. 4, FIG. 8: shows as an enlarged side view the hand piece part according to FIG. 3 in the region of the hand piece tip.

In the case of the modification of the hand piece parts 5 shown here, the depth of the filling chamber 2 to the filling-chamber base 13 is less than in the case of the exemplary embodiment according to FIG. 3. The head-guiding groove 14 between the entry region 15 and the hand piece tip 3 is curved in a region of the delivery portion 19 adjoining the filling chamber 2, in order to avoid jamming of items introduced.

FIG. 14

The hand piece 1 with its two hand piece parts 5 has been placed, with its outer side lying opposite the filling chamber 2, onto a substantially horizontally aligned bearing surface 29. Protruding into the filling chamber 2 is an opened side of a supply container 30, such as a plastic bag or plastic box, filled with screws 20. Some of the screws 20 are already arranged in the filling-chamber base 13 of the filling chamber 2 due to the oblique-wall portions 10 of the bottom inner edge 11 and lie with their screw heads 21 in the head-guiding grooves 14. The screw shanks 22 of some of these screws 20 have already entered the shank-guiding recesses 17.

FIG. 15

The screws 20, with which the filling chamber 2 has been filled, are now brought into a position by a back and forth movement along the bearing surface 29, as indicated by arrow 31. In this position, all the screw shanks 22 have entered the shank-guiding recesses 17.

FIG. 16

The hand piece 1 is now in a position tilted with respect to the bearing surface 29. Following the downgrade force, the screws 20 have entered the delivery portion 19 of the head-guiding grooves 14.

FIG. 17

Seen here is the tip region 3 of the hand piece 1 with the region of the delivery portion 19 adjoining the end portion 18, in which region the screws 20 are arranged following one another. The hand piece 1 is arranged here substantially at right angles with respect to a substantially horizontally lying screw-receiving part 32, which has a number of regularly spaced-apart screw-receiving recesses 33, into which the screws 20 are to be introduced by their screw shanks 22. The screw 20 furthest forward in the direction of the end portion 18 has been tilted by its screw head 21 from the delivery portion 19 into the blind continuation 23 and into the depression 24 of the end portion 18. The subsequent screws 20 lie with a certain tilt with respect to the horizontal in the delivery portion 19. The forwardmost screw 20 blocks by its screw head 21 further following on of the subsequent screws 20. The screw shank 22 of the forwardmost screw 20 has already been partially inserted into a screw-receiving recess 33 of the screw-receiving part 32.

FIG. 18

Figure 17:
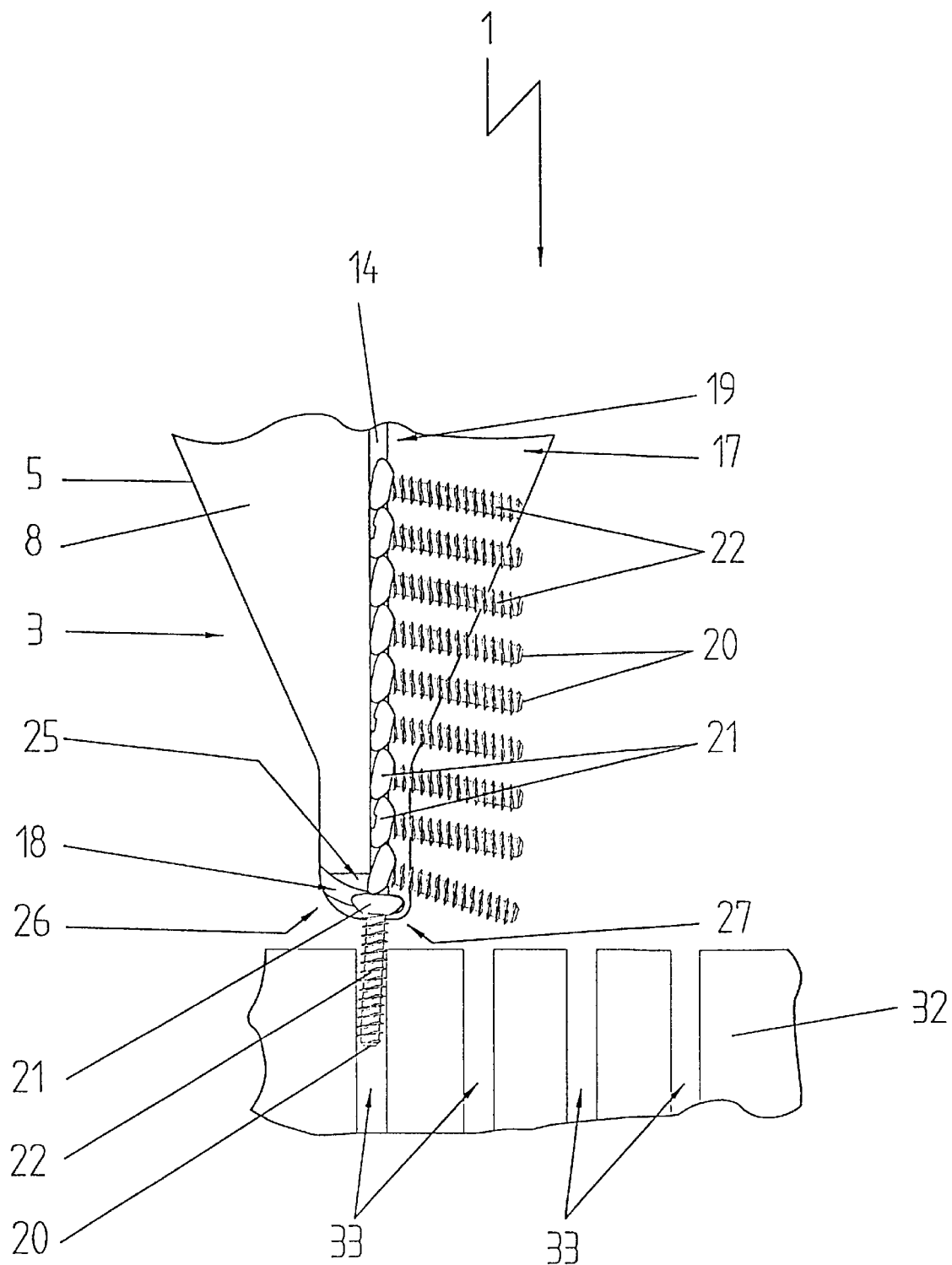

Here, the hand piece 1 is in a position tilted right over with respect to the vertical. The forwardmost screw 20 is in the outlet region of the end portion 18 pointing away from the delivery portion 19, where the dispensing block has already been overcome by manual rolling-like handling of the hand piece 1, while at the same time fixing the screw shank 22 in the screw-receiving recess 33. On account of the tilting of the hand piece 1 right over with respect to the vertical, the screw head 21 of the screw 20 has for the most part already left the end portion 18 of the head-guiding groove 14. The next-following screw 20 still has its screw head 21 clamped in the transitional region between the delivery portion 19 and the end portion 18. After drawing the hand piece 1 away from the screw head 21 of the screw 20 inserted into a screw-receiving recess 33 and a renewed, substantially vertical aligning of the hand piece 1, the next screw 20 slips into the position according to FIG. 17. Consequently, the screw-receiving part 32 can be provided with this next screw 20.

FIG. 19

Now, the head-guiding groove 14 is free of screws 20 and the hand piece 1 has been tipped right over with respect to the vertical. The screw head 21 of a wrongly inserted screw 20—with a shorter screw shank 22 in comparison with neighbouring screws 20—is arranged in the end region of the end portion 18 lying opposite the delivery portion 19 and has already partially entered the said region.

FIG. 20

Figure 18:
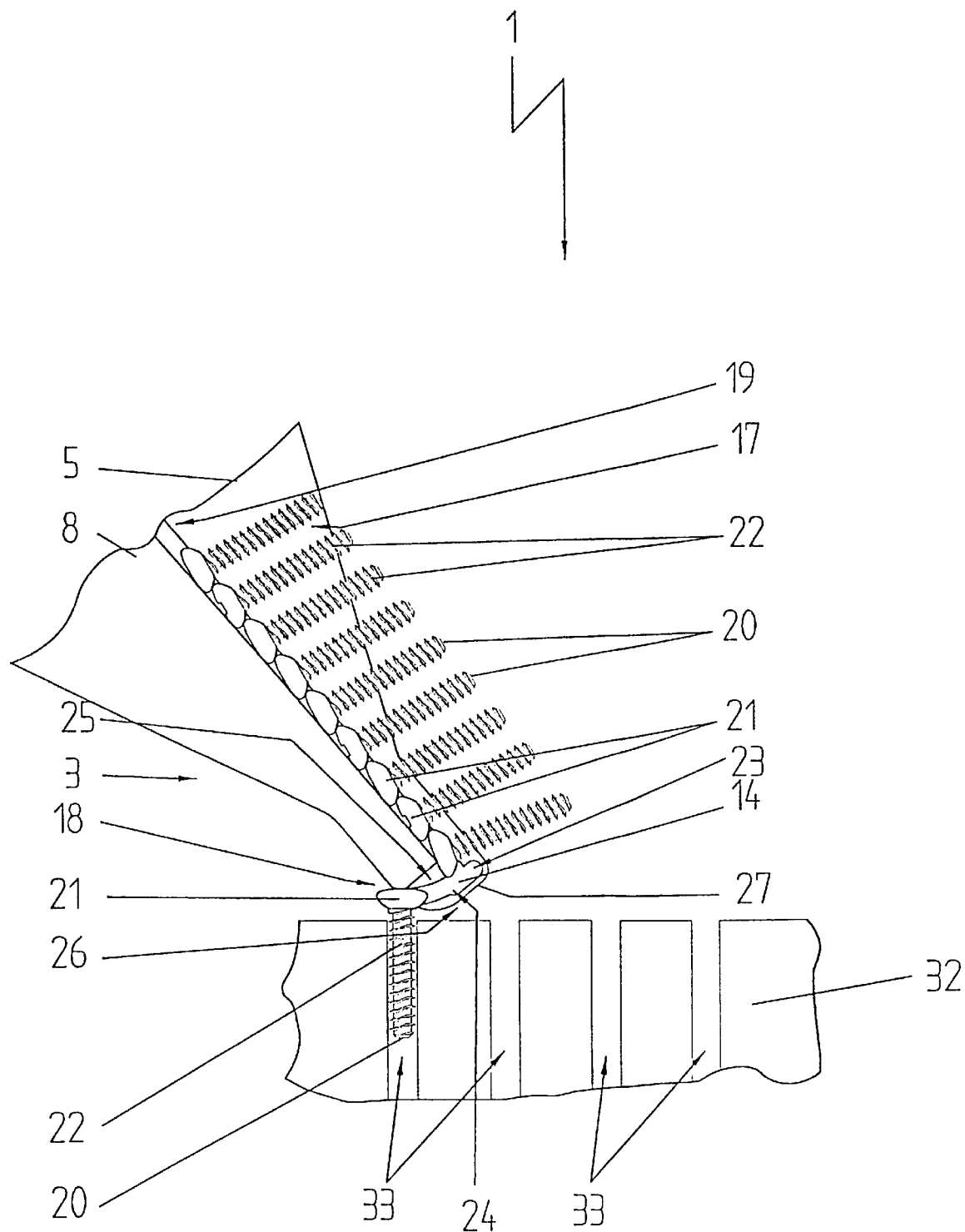
Figure 19:
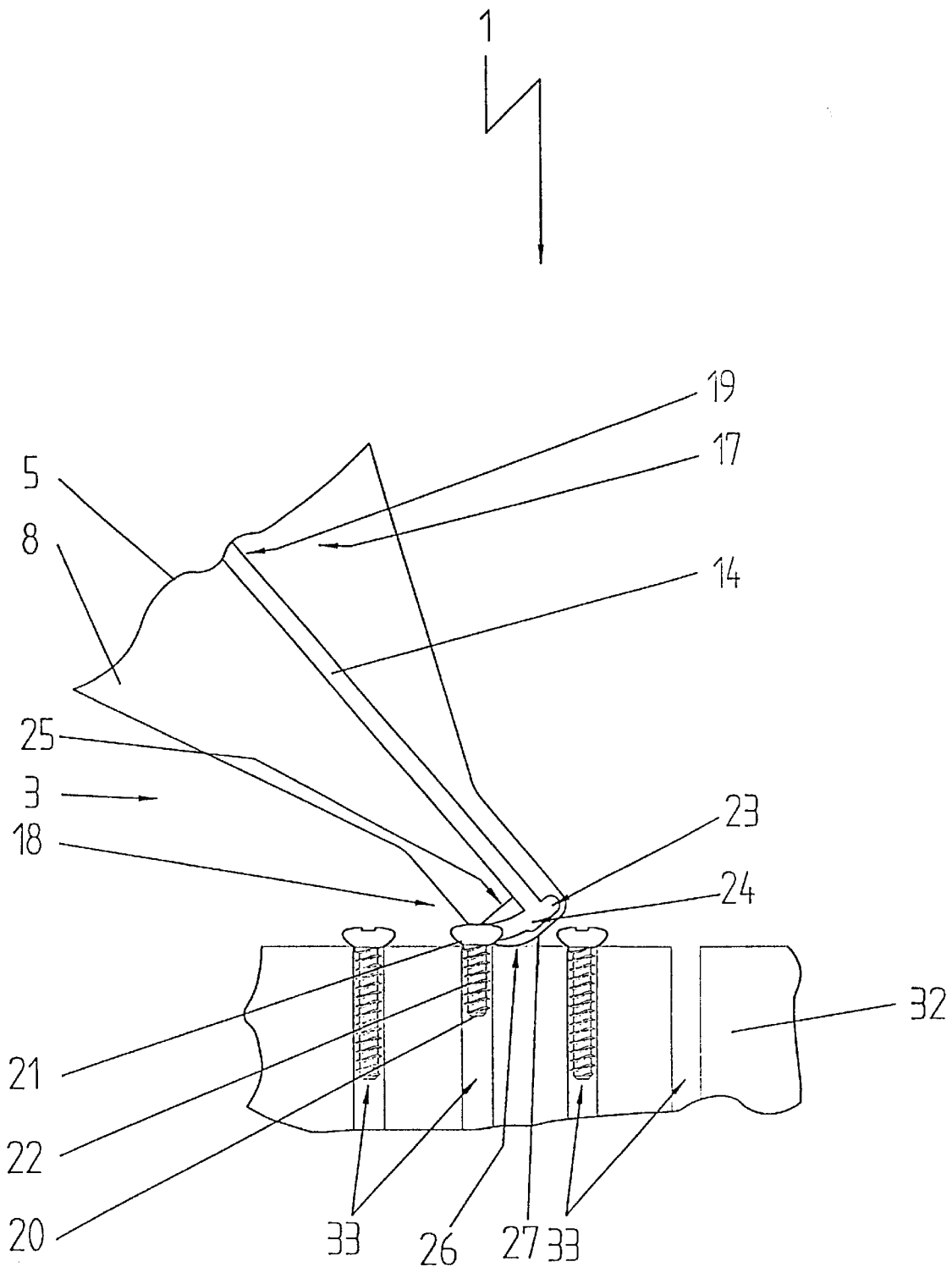
FIGS. 19 and 20: show as a side view a hand piece part for explaining the handling of the hand piece according to FIG. 1 when receiving screws from a screw-receiving part.
Figure 20:
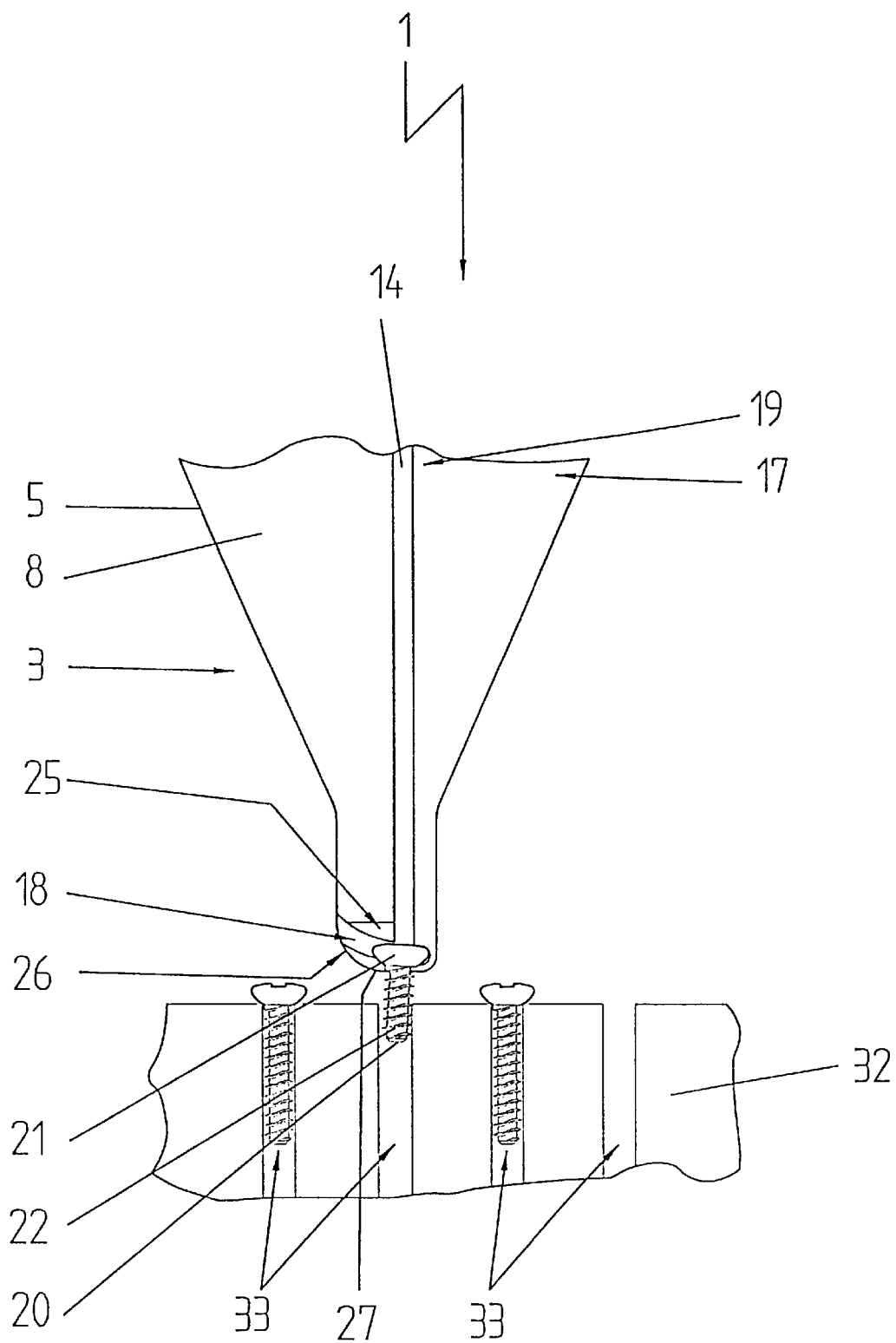

The hand piece 1 is in a vertical position aligned substantially at right angles to the screw-receiving part 32 and lifted off the screw-receiving part 32. The screw 20 with the shorter screw shank 22 has entered with its screw head 21 into the depression 24 and the blind continuation 23 in the transitional region between the end portion 18 and the delivery portion 19 of the head-guiding grooves 14. In this arrangement, the screw 20 is securely held and can be removed from the screw-receiving part 32, and can, for example, be correctly inserted into another screw-receiving part 32 in a way corresponding to the procedure explained with respect to FIGS. 17 to 19.

What is claimed is:

1. Device for handling items (20) with a head (21), a shank (22) and a solid outer contour, comprising:
    a) a hand piece (1), which has a chamber (2) with a base (13) for receiving the items (20),
    b) there extending from the inner side (11) of the chamber (2) to a dispensing side (3) of the hand piece (1) a guiding recess (14, 17), which has a cross-section adapted to the outer contour of the items (20) and has at the end of the dispensing side an end portion (18) which is angled away with respect to a delivery portion (19) adjoining the chamber (2), characterized in that the end portion (18)
    c) in the region adjoining the delivery portion (19), is oriented at an acute angle with respect to the delivery portion (19); and
    d) runs at an inclination counter to the feeding direction of an item (20) from the chamber (2) into the front region of the delivery portion (19) adjoining the end portion (18), thus in the direction of the delivery portion (19).

2. Device according to claim 1, characterized in that the end portion (18) is curved in the direction of the delivery portion (19).

3. Device according to claim 1 or 2, characterized in that
    a) in the transitional region between the delivery portion (19) and the end portion (18) there is formed a continuation (23) extending away from said dispensing side (3) in prolongation of the end portion (18) and terminating in a dead-end; and b) the end portion (18) has in the region where it meets the delivery portion (19) a depression (24) lying opposite the delivery portion (19).

4. Device for handling items (20) with a head (21), a shank (22) and a solid outer contour, comprising:
   a) a hand piece (1), which has a chamber (2) with a base (13) for receiving the items (20),
   b) there extending from an inner side (11) of the chamber (2) to a dispensing side (3) of the hand piece (1) a guiding recess (14, 17), which has a cross-section adapted to the outer contour of the items (20) and has at the end on the dispensing side an end portion (18) which is angled away with respect to a delivery portion (19) adjoining the chamber (2), characterized in that
   c) the end portion (18), in a region adjoining the delivery portion (19), is aligned at right angles with respect to the delivery portion (19); and
   d) in the transitional region between the delivery portion (19) and the end portion (18), a continuation (23) extending in prolongation of the end portion (18) is provided as a head-engaging means.

5. Device for handling items (20) with a head (21), a shank (22) and a solid outer contour, comprising:
   a) a hand piece (1), which has a chamber (2) with a base (13) for receiving the items (20),
   b) there extending from an inner side (11) of the chamber (2) to a dispensing side (3) of the hand piece (1) a guiding recess (14, 17), which has a cross-section adapted to the outer contour of the items (20) and has at the end on the dispensing side an end portion (18) which is angled away with respect to a delivery portion (19) adjoining the chamber (2), characterized in that
   c) the end portion (18), in a region adjoining the delivery portion (19), is aligned at right angles with respect to the delivery portion (19); and
   d) in the transitional region between the delivery portion (19) and the end portion (18), a depression (24) lying opposite the delivery portion (19) is provided as a head-engaging means.

6. Device for handling items (20) with a head (21), a shank (22) and a solid outer contour, comprising:
   a) a hand piece (1), which has a chamber (2) with a base (13) for receiving the items (20),
   b) there extending from an inner side (11) of the chamber (2) to a dispensing side (3) of the hand piece (1) a guiding recess (14, 17), which has a cross-section adapted to the outer contour of the items (20) and has at the end on the dispensing side an end portion (18) which is angled away with respect to a delivery portion (19) adjoining the chamber (2), characterized in that
   c) the end portion (18), in a region adjoining the delivery portion (19), is aligned at right angles with respect to the delivery portion (19); and
   d) in the transitional region between the delivery portion (19) and the end portion (18), a continuation (23) extending in prolongation of the end portion (18) and a depression (24) lying opposite the delivery portion (19) are provided as a head-engaging means.

7. Device according to one of claims 1 or 4 or 5 or 6, characterized in that
   a) in the transitional region between the delivery portion (19) and the end portion (18) there is provided a transitional recess (25); and
   b) between the delivery portion (19) and the end portion (18) there is provided a curved transitional portion (28).

8. Device according to one of claims 1 or 4 or 5 or 6, characterized in that
   a) with its part (17) receiving the shanks (22) of the items (20), the guiding recess (14,17) is open with respect to the outer side of the hand piece (1) lying opposite the chamber (2); and
   b) the guiding recess (14,17) enters the base (13) of the chamber (2) and extends over the base (13) of the chamber (2).

9. Device according to claim 8, characterized in that
   a) the chamber (2) has a wall (9,10) which, at least in the region of the base (13), is formed at an acute angle; and
   b) in the entry region (15) into the chamber (2), the guiding recess (14,17) is widened in cross-section by means of a rounding-off (16).

10. Device according to one of claims 1 or 4 or 5 or 6, characterized in that the hand piece (1) is made up of two hand piece parts (5) which can be fitted together, the guiding recess being formed by head-guiding grooves (14), for receiving the heads (21), and shank-guiding recesses (17), for receiving the shanks (22) of the items (20), provided in the hand piece parts (5).

11. Device according to one of claims 1 or 4 or 5 or 6, characterized in that
   a) the hand piece (1) is of an elongated design and the dispensing side (3) is tapered in a tip-like manner; and
   b) the chamber (2) can be closed by a cover (6).

12. A portable dispenser for controlled dispensing of a plurality of items (20) with a head (21) and a shank (22) to a receiver, comprising:
   a housing (1) having an internal chamber (2) for receiving the items (20), said housing having a dispensing end (3) from which said items are dispensed, said housing having a guiding recess (14, 17) extending from said internal chamber (2) to said dispensing end (3), said guiding recess (14, 17) having a cross-sectional shape approximating the outer contour of the items (20) and accommodating the items (20) therein to permit the passage of the items (20) from said internal chamber (2) to said dispensing end (3), said guiding recess (14, 17) having a delivery portion (19) adjoining said internal chamber (2) into which said items (20) are received from said internal chamber (2) and an end portion (18) disposed proximate said dispensing end (3) and contiguous with said delivery portion (19) distal to said internal chamber (2), said delivery portion (19) delivering said items (20) from said chamber (2) to said end portion (18) in said dispensing end (3), said end portion (18) sequentially holding the items (20) in a selected alignment relative to the receiver to allow the insertion of the shank (22) of each of the items (20) into the receiver and permitting each of the items to be dispensed from said dispenser by tilting the dispenser to a selected orientation and withdrawing the dispenser away from the item, said end portion (18) being oriented relative to said delivery portion (19) such that the angle at the junction therewith is generally less than or equal to 90 degrees.

13. The dispenser of claim 12, wherein said end portion (18) is oriented relative to said delivery portion (19) to form an L shape, with the delivery portion (19) being the longer, upper portion of the L and the end portion (18) being the shorter, lower portion of the L.

14. The dispenser of claim 13, wherein said end portion (18) is laterally shifted relative to said delivery portion (19)

such that the delivery portion (19) discharges into said end portion (18) intermediate the ends of said end portion, one end of said end portion being open to dispense said items and the other end being closed.

15. The dispenser of claim 12, wherein said end portion (18) is shaped and oriented relative to said delivery portion (19) to form a J shape, with the delivery portion (19) being the longer, upper portion of the J and the end portion (18) being the shorter, curved, lower portion of the J.

16. The dispenser of claim 15, wherein said end portion (18) is laterally shifted relative to said delivery portion (19) such that the delivery portion (19) discharges into said end portion (18) intermediate the ends of said end portion, one end of said end portion being open to dispense said items and the other end being closed.

17. The dispenser of claim 12, wherein said end portion (18) includes a recess (25) for accommodating the heads (21) of the items (20), said recess being positioned proximate the juncture between said delivery portion (19) and said end portion (18) to receive the heads (21) when the items are held in said selected alignment relative to said receiver.

18. The dispenser of claim 12, wherein said angle at said junction is radiused (28).

19. A portable dispenser for controlled dispensing of a plurality of items (20) with a head (21) and shank (22) to a receiver, comprising:

a housing (1) having an internal chamber (2) for receiving the items (20), said housing having a dispensing end (3) and an opening therein from which said items are dispensed, said housing having guiding means extending from said internal chamber to said opening in said dispensing end for permitting the passage of the items (20) from said internal chamber (2) to said opening in said dispensing end (3) under the influence of gravity as controlled by the position of said housing, said guiding means sequentially holding the items with the shank (22) projecting from said opening in said dispensing end (3) in a selected orientation relative to the housing (1) to allow the insertion of the shank (22) of each of the items (20) into the receiver and permitting each of the items to be dispensed from said dispenser by tilting the dispenser to a selected orientation and withdrawing the dispenser away from the item.

\* \* \* \* \*